United States Patent [19]
Cumming

[11] Patent Number: 6,051,024
[45] Date of Patent: *Apr. 18, 2000

[54] INTRAOCULAR LENSES WITH FIXATED HAPTICS

[76] Inventor: J. Stuart Cumming, 1407 Emerald Bay, Laguna Beach, Calif. 92656

[*] Notice: This patent is subject to a terminal disclaimer.

[21] Appl. No.: 08/947,113

[22] Filed: Oct. 8, 1997

Related U.S. Application Data

[63] Continuation-in-part of application No. 08/540,040, Oct. 6, 1995, abandoned.

[51] Int. Cl.[7] .................................. A61F 2/16; A61F 2/14
[52] U.S. Cl. ........................................ 623/6; 623/4
[58] Field of Search ............................ ; A61F 2/16, 2/14

[56] References Cited

U.S. PATENT DOCUMENTS

| | | | |
|---|---|---|---|
| 4,813,953 | 3/1989 | Sheets | 623/6 |
| 5,013,322 | 5/1991 | Rosa | 623/6 |
| 5,258,025 | 11/1993 | Fedorov et al. | 623/6 |
| 5,476,514 | 12/1995 | Cumming | 623/6 |
| 5,578,081 | 11/1996 | McDonald . | |
| 5,716,403 | 2/1998 | Tran et al. | 623/6 |
| 5,843,188 | 12/1998 | McDonald | 623/6 |

*Primary Examiner*—David H. Willse
*Assistant Examiner*—Dinh X. Nguyen
*Attorney, Agent, or Firm*—Boniard I. Brown

[57] ABSTRACT

Intraocular lenses for implanting within natural capsular bags of human eyes have features on distal end portions to prevent movement or sliding thereof relative to fibrosis pockets or tunnels defined about proximally adjacent haptic portions to fixate haptics against dislocation.

9 Claims, 4 Drawing Sheets

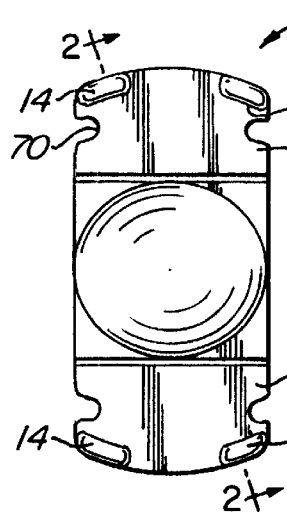
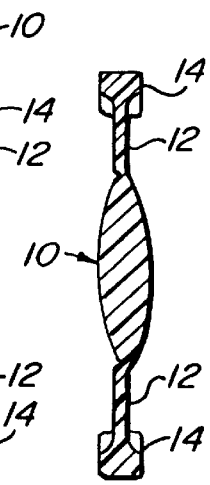
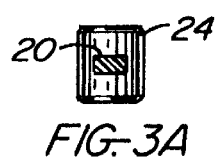
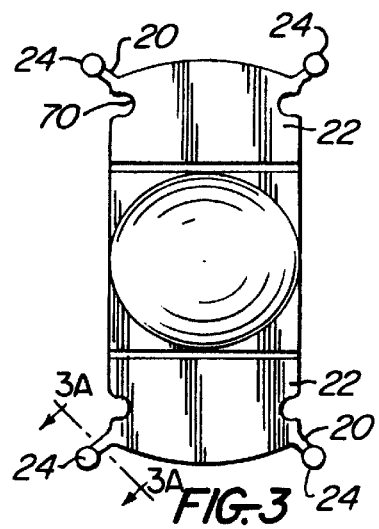
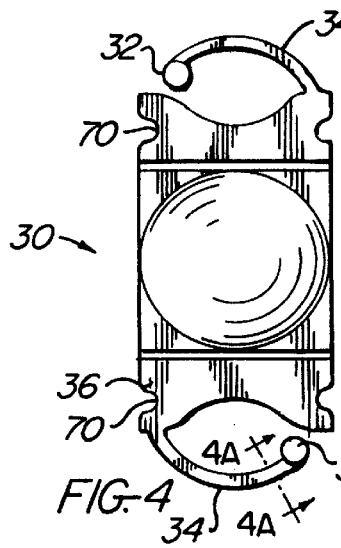
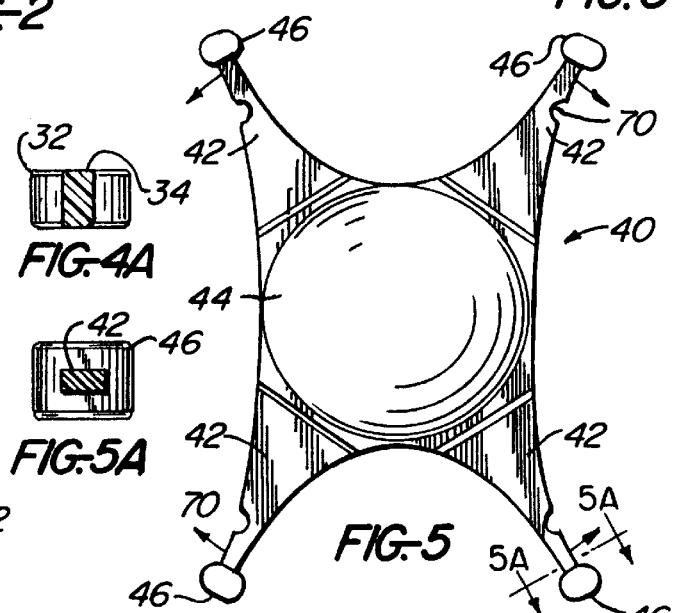
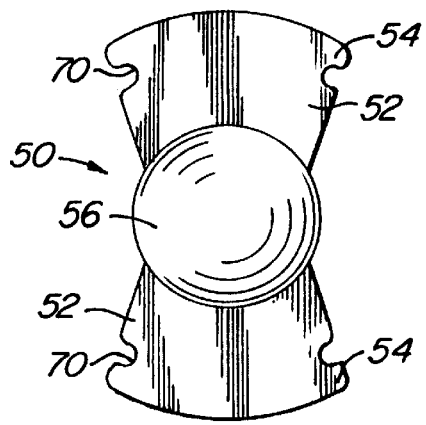
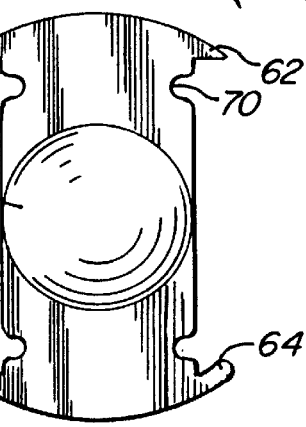

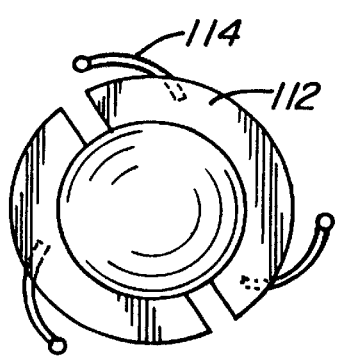
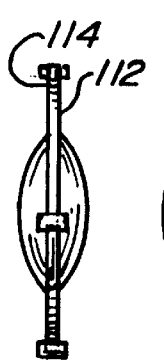
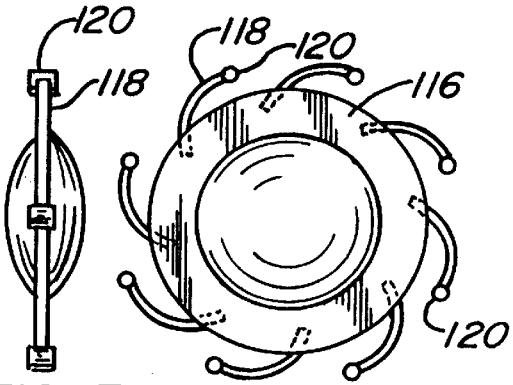
FIG.-16  FIG.-16A  FIG.-17A  FIG.-17
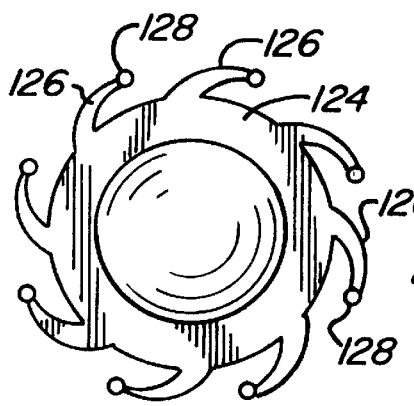
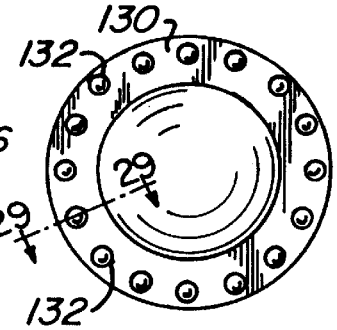
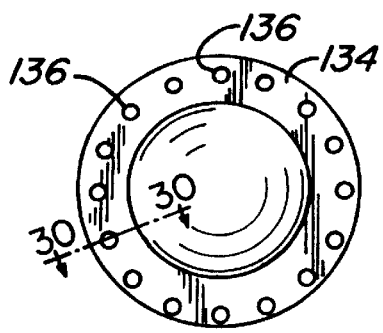
FIG.-18  FIG.-19  FIG.-20
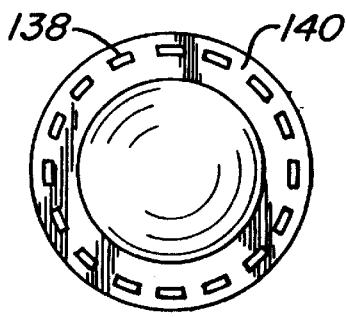
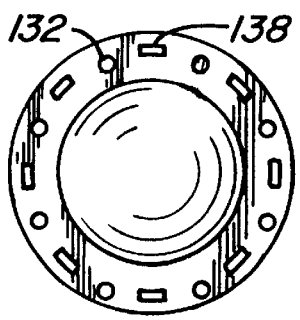
FIG.-21  FIG.-22

INTRAOCULAR LENSES WITH FIXATED HAPTICS

RELATED APPLICATIONS

This application is a continuation-in-part of my application Ser. No. 08/540,040, filed Oct. 6, 1995 now abandoned.

BACKGROUND OF THE INVENTION

In cataract surgery, the practice is to remove the cataractous natural lens and replace it with a man-made lens. The replacement lens is placed inside the natural capsular bag of the natural human lens. Such replacement of the natural lens by artificial intraocular lens is discussed in my U.S. Pat. Nos. 5,476,514 and 5,047,051.

The present invention represents improvements over my above-mentioned patents relative to the fixation or anchoring of the lens haptics in the bag, thereby overcoming certain potential disadvantages of plate haptic lenses. My U.S. Pat. No. 5,047,051 discloses a method of fixing a haptic plate in the capsular bag by means of mini-loops at the ends of haptic anchor plates. This enables the bag to fibrose about the loops to fix the lens in the bag.

In such procedures, plate haptic lenses without loops or fixation means can only be implanted in an intact capsular bag with a continuous circular capsulotomy. Such plate haptic lenses, if placed into a capsular bag having a tear in the anterior capsular rim or posterior capsule, can dislocate with resultant serious complication of the surgery.

During the healing and fibrosis process, the anterior capsule rim becomes fused to the posterior capsule by fibrosis, and a plate haptic with an appendage thereof is retained in position by a pocket or tunnel defined by the fibrosis about the haptic or appendage portions between the anterior capsular rim and the posterior capsule.

SUMMARY OF THE INVENTION

As discussed in the foregoing background, a haptic is retained in place by a pocket or tunnel defined in fibrosis about haptic and appendage portions between the anterior capsular rim and the posterior capsule.

The fibrosis fuses together the anterior and posterior capsules, and surrounds portions of a plate haptic.

Plate haptic lenses are sometimes desirable because they provide certain advantages over long loop lenses, including stabilization of the vitreous with substantially less probability of the most serious complications of cataract surgery, these being retinal detachment and cystoid macular edema. Another advantage is the consistent posterior location of the optic, which not only stabilizes the vitreous, but provides more predictable post-operative, uncorrected visual acuity. A further advantage is that the posterior location of the lens results in tight contact of the lens with the posterior capsule, thereby resulting in reduced rate of opacification of the posterior capsule with resultant reduced posterior capsulotomy rate.

Improved accommodating intraocular lenses according to the invention include a central optic having normally anterior and posterior sides and extended portions spaced circumferentially about and extending generally radially out from the edge of the optic. These extended portions have inner ends joined to the optic and opposite outer ends movable anteriorly and posteriorly relative to the optic.

The lens is surgically implanted in the evacuated capsular bag of the lens of an eye through the anterior capsule opening in the bag in a position wherein the lens optic is aligned with the opening defined by the anterior capsular remnant, and the outer ends of the lens distal portions are disposed within the outer perimeter or cul-de-sac of the bag. The lens has a radial dimension from the outer end of each distal or extended portion to the axis of the lens optic so that with the lens implanted within the capsular bag, the outer ends of the extended portions engage the inner perimetrical wall of the bag with no or minimal stretching of the bag.

After implantation of the accommodating intraocular lens in the capsular bag, active ectodermal cells on the posterior surface of the anterior capsule rim of the bag cause fusion of the rim to the elastic posterior capsule of the bag by fibrosis about the lens extended portions in such a way that these portions are effectively "shrink-wrapped" by the fibrous tissue so as to form radial pockets or tunnels in the fibrous tissue which contain the haptic portions with their distal ends positioned within the cul-de-sac of the capsular bag. The lens is thereby fixated within the capsular bag with the lens optic aligned with the opening in the anterior capsular bag. The anterior capsule rim shrinks during fibrosis, and this, combined with fibrosis about the extended portions, causes some radial compression of the lens so as to tend to move the optic relative to the outer ends of the extended portions in one direction or the other along the optic axis. The fibrosed, leather-like anterior capsule rim prevents anterior movement of the optic and urges it rearwardly during fibrosis. Accordingly, fibrosis induced movement of the optic occurs posteriorly to a distant vision position wherein either or both the optic and the inner ends of the extended portions press rearwardly against and stretch the elastic posterior capsule rearwardly.

During surgery, the ciliary muscle of the eye is paralyzed with a ciliary muscle relaxant, i.e., a cycloplegic, such as atropine, to place the muscle in its relaxed state. Following surgery, a ciliary muscle relaxant is periodically introduced throughout a post-operative fibrosis and healing period (such as two to three weeks) to maintain the ciliary muscle in its relaxed state until fibrosis is complete. This drug-induced relaxation of the ciliary muscle prevents contraction thereof and immobilizes the capsular bag. By this means, the lens optic is fixed during fibrosis in its distant vision position within the eye relative to the retina and the lens presses rearwardly against and thereby posteriorly stretches the elastic posterior capsule of the capsular bag. If the ciliary muscle was not thus maintained in its relaxed state until the completion of fibrosis, the ciliary muscle would undergo essentially normal brain-induced vision accommodation contraction and relaxation during fibrosis, and the intraocular lens would not necessarily fix in the distant position but in some other location along the axis of the eye.

The present invention provides haptic lens features which serve to fixate the distal haptic portions of the lens, thus preventing dislocation and slipping from the proper positions in pockets or tunnels formed over the haptic lens features by fibrosis. Enlarged and/or distal haptic portions or protuberances are prevented by their larger dimension from moving or sliding along pockets or tunnels formed by fibrosis about proximally inward haptic portions. The enlarged distal structural features prevent the haptic from sliding inwardly relative to such fibrosis pockets to fixate and prevent dislocation of the intraocular lens. The enlarged distal structural features may take such forms as: protuberances extending from one or both sides of distal portions of plate haptics; flexible extensions extending from distal corners of lens plate haptics, which extensions may have protuberances; protuberances extending outwardly from spring loops or filamentary loops; enlarged end portions or protuberances on distal portions of a plurality of haptics extending from their proximal ends at an optic; enlarged wide distal portions of haptics tapered to widen in the distal direction; prong protuberances extending laterally outwardly from distal portions of haptics; and notches in side edges of distal portions of haptics.

Other preferred embodiments of the invention include extended or distal protuberances or knobs and openings defined in distal portions of haptics, which serve to fixate the distal haptic portions in the periphery of the capsular bag between the posterior bag and the anterior capsule remnant by the fibrosis process described in the foregoing Background of the Invention, by the prevention of relative movement of the distal portions of the haptics relative to pockets or tunnels formed by fibrosis about proximately inward haptic portions. Other preferred embodiments also include flexible loop haptics extending from disk haptic portions, knobs provided in the distal portions of a disk haptic element, openings provided in the distal portions of a disk haptic element, and knobs and/or openings provided in the distal portions of a plurality of plate-type haptics extending from the optic to their distal edge portions.

BRIEF DESCRIPTION OF THE DRAWINGS

FIG. 1 is an elevational view of a preferred embodiment of the invention, showing a plate haptic lens with enlarged protuberances at its distal corners;

FIG. 2 is a sectional view taken at 2—2 in FIG. 1;

FIG. 3 is an elevational view of an embodiment of the invention wherein flexible extensions with protuberances extend diagonally outwardly from distal corners of haptic plates;

FIG. 3A is a sectional view taken at 3A—3A in FIG. 3;

FIG. 4 is an elevational view of a haptic plate lens with spring loops extending outwardly with enlarged portions or protuberances on the loops;

FIG. 4A is a sectional view taken at 4A—4A in FIG. 4;

FIG. 5 illustrates an embodiment of the invention wherein a plurality of symmetrically tapered haptics extend from wide proximal ends joined by an optic to relatively narrow distal ends whereon protuberances are disposed;

FIG. 5A is a sectional view taken at 5A—5A in FIG. 5;

FIG. 6 is a perspective view of an embodiment wherein each of oppositely-extending haptics has a distal portion wider than inward or proximal haptic portions;

FIG. 7 is an elevational view of an embodiment of the invention wherein are shown in partial views two forms of prong protuberances extending laterally outwardly from distal portions of oppositely extending haptics;

FIGS. 16 and 16A show elevational and side views of an embodiment wherein a disk haptic element has extending therefrom a plurality of flexible loop haptics;

FIGS. 17 and 17A illustrate an elevational and side views of an embodiment wherein a disk haptic element has extending therefrom a plurality of flexible loop haptics having knobs at their outer or distal ends;

FIG. 18 shows an embodiment wherein a disk haptic member has defined in its periphery a plurality of inclined or somewhat tangential prong portions having knobs or protuberances at their ends;

FIG. 19 is an embodiment having a disk haptic member with a plurality of knobs or protuberances disposed about its distal edge portion;

FIG. 20 is an embodiment wherein a disk haptic member has a plurality of generally circular openings disposed in its distal edge portions;

FIG. 21 shows an embodiment wherein a disk-shaped haptic member has a plurality of slot openings in its distal edge portion;

FIG. 22 is an embodiment wherein a disk-shaped haptic member has alternating slot openings and knobs disposed in and on its peripheral distal portion;

DESCRIPTION OF PREFERRED EMBODIMENTS

Figure 8A:
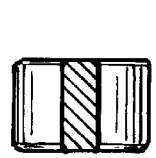
FIG. 8A is a sectional view taken at 8A—8A in FIG. 8.

The present invention provides distal features of haptics of intraocular lenses which serve to fixate the haptic distal portions in the periphery or cul-de-sac between posterior capsule and anterior capsular bag remnant of the capsular bag. The fibrosis process and procedure for effecting fibrosis about haptic portions are discussed hereinbefore in the Background of the Invention.

It is important that distal portions of haptic means be fixated in the periphery of the capsular bag between an anterior capsular remnant and the posterior capsule, and that such distal portions or features not move relative to pockets or tunnels defined by fibrosis about distal haptic features.

With relatively constant movement of lens haptics on optics, there can be disengagement of distal haptic portions relative to the bag periphery between the posterior bag and anterior remnant, if adequate retention is not provided. Such disengagement of continued operational force can result if adequate fixation is not provided, and can result from such factors as capsular bag shrinkage during fibrosis causing a tear to occur in the capsular bag, thus possibly resulting in lens dislocation and the haptic being then positioned in the vitreous in the posterior portion of the eye, with serious complications.

The embodiments of the present invention herein described provide distal haptic features which prevent dislocation of haptics by slipping or shifting of distal haptic portions or features relative to fibrosis pockets or tunnels wherein distally inward portions of the haptics are disposed.

Referring to the drawings, and particularly to FIG. 1, a preferred embodiment 10 has a distal portion of a plate haptic 12 with protuberances 14 thereon. The sectional view of FIG. 2 shows the configuration of the protuberances which extend from both sides of haptic 12. A protuberance may extend from only one side or surface of the haptic. The protuberances will not pass or slide through a fibrosis tunnel or pocket disposed about proximally adjacent smaller dimensioned portions of the haptic.

FIGS. 3 and 3A illustrate an embodiment wherein flexible extensions 20 extend diagonally from distal corners of lens plate haptics 22, and have protuberances 24 at their ends. Extensions 20 position the protuberances laterally and distally outwardly of the edges of the haptic, so that they are prevented from moving or sliding through a pocket defined by fibrosis about the proximally inward portions of the haptics. FIG. 3A shows the cross-sectional configuration of the protuberances.

FIGS. 4 and 4A illustrate an embodiment 30 wherein protuberances 32 extend outwardly from spring loops or fingers 34 which extend from distal portions of plate haptics 36. The protuberances 32 prevent the loop and the distal portions of the haptic plates from moving or sliding relative to fibrosis pockets formed about the loop and distal haptic portions. FIG. 4A shows in cross-section the configuration of the protuberances at the ends of the loops. A lens (not shown) generally similar to that of FIG. 4, may have a loop element attached to a haptic plate, as by fusion or adhesure, rather than being integrally formed with the plate.

FIG. 5 illustrates an embodiment 40 of the invention wherein a plurality of haptics 42 are symmetrically tapered outwardly from relatively wide proximal ends joined to an optic 44 to relatively narrow distal ends or fingers whereon protuberances 46 are disposed. FIG. 5A shows protuberance details.

FIG. 6 illustrates an embodiment 50, which is not an accommodation lens, wherein each of plate haptics 52 has a wider distal protuberance portions 54 than proximally adjacent haptic portions. Distal protuberance portions of the haptics are defined by tapered haptic configurations which widen in the distal direction. The wider distal haptic portion prevents movement of the haptic toward the optic being retained against movement relative to the pocket defined by fibrosis about the plate haptic inwardly of the distal portion.

FIG. 7 illustrates another embodiment 60 of the invention wherein prong protuberances 62, with prongs 64 with rounded ends, extend laterally outwardly from distal portions of plate haptics extending from an optic 66. The prong protuberances 62 effectively prevent proximal movement toward optic 66 by inward portions of the haptics relative to the fibrosis pockets formed about proximally inward portions of the haptics.

FIGS. 1, 3 and 4 to 7 illustrate embodiments of the invention wherein notches 70 are defined in distal edge portions of plate haptics. Preferably, a notch 70 is defined in both lateral distal edge portions of a haptic, and such notches are preferably defined in lateral edges of the distal portions of at least two haptics extending in different directions from an optic. As shown, the notch 70 typically has an edge portion disposed at a substantial angle to or substantially transversely of the side edge or longitudinal axis of the haptic. Such notches and edge portions are thus disposed to prevent the haptics from becoming dislocated by preventing shifting or sliding thereof relative to fibrosis pockets in which proximally inward haptic portions are disposed.

FIGS. 8 through 30 illustrate embodiments of the invention which provide protuberances, knobs, openings or haptic means in distal portions for fixating haptics in the periphery of the capsular bags between the posterior bags and the anterior capsular remnants.

Figure 8:
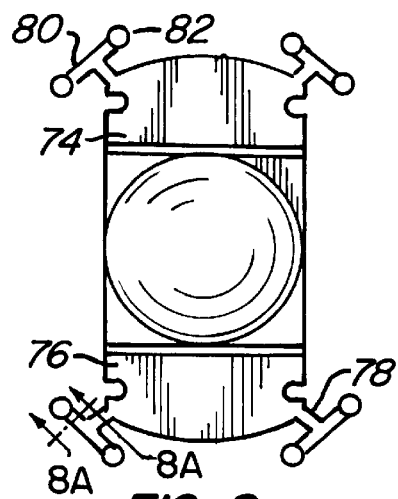
FIG. 8 is an elevational view of an embodiment similar to that of FIG. 3, but differing in having distal cross-portions at a diagonal extension on each corner, at each end of which is disposed a protuberance or knob.

FIG. 8 illustrates an embodiment somewhat similar to that of FIG. 3, wherein there extend from plate haptic portions 74, 76 extensions 78 and cross portions 80 at either end of each of which is a knob or protuberance 82, shown in cross-section in FIG. 8A, each extending anteriorly and posteriorly of the plate haptic portion. These protuberances are well-positioned for engagement in the peripheral portion or cul-de-sac of the capsular bag between the posterior bag and anterior remnant, thus to prevent haptic movement through any tunnel or pocket defined by fibrosis about proximately inward haptic portions.

Figure 9:
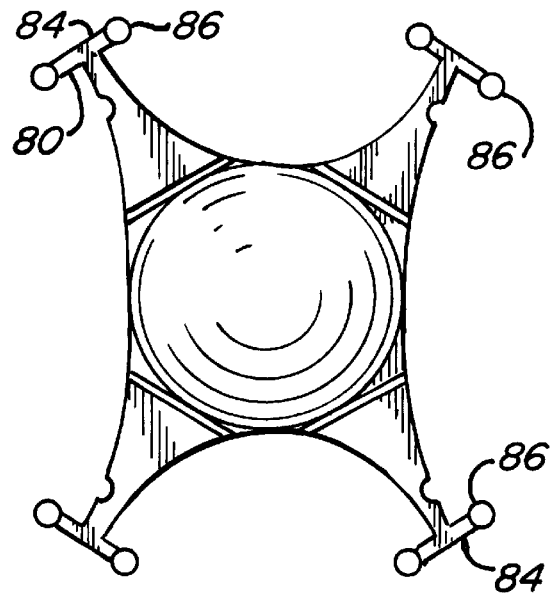
FIG. 9 is an embodiment similar in certain respects to that of FIG. 5 and differing therefrom in having cross-portions extending from the end of each of the symmetrically tapered haptic portions, each cross-member having a knob or protuberance at each of its ends.

FIG. 9 shows an embodiment with a general configuration somewhat similar to FIG. 5, with transverse cross-portions 84 extending from the outer ends of each symmetrically tapered haptic, and having disposed at each end of each cross-portion a knob 86. These protuberances are well-adapted to extend into the peripheral portion of the capsular bag between anterior remnant and posterior bag to fixate the haptic.

Figure 10:
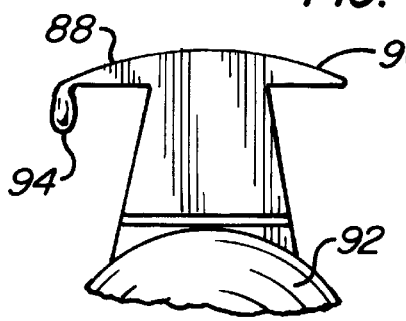
FIGS. 10 and 11 are related embodiments having plate-type haptics extending in opposite directions from an optic, and having extending therefrom step portions from which extend or are mounted knobs or protuberances.
Figure 11:
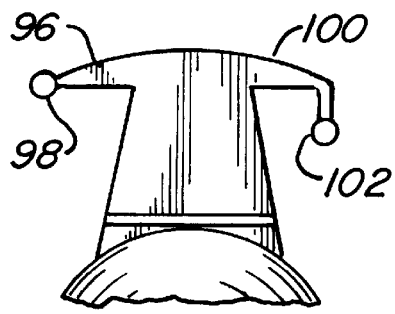

FIGS. 10 and 11 illustrate embodiments wherein step portions 83, 90 (FIG. 10) are adapted to engage in the peripheral bag portion between the anterior capsular rim and the posterior capsule, there being similar haptic portions (not shown) at the opposite side of the optic 92. A protuberance or knob 94 depends from step 88 and extends anteriorly and posteriorly. The steps and the knob 94 are adapted to be engaged by fibrosis to fixate the haptic and prevent inward movement of these components. In the FIG. 11 embodiment, step 96 has on its outer end portion a knob or protuberance 98, and step 100 has depending from its outer end portion an arm from which depends a knob or protuberance 102, the knobs of FIG. 11 serving purposes similar to those of the knob of FIG. 10.

Figure 12:
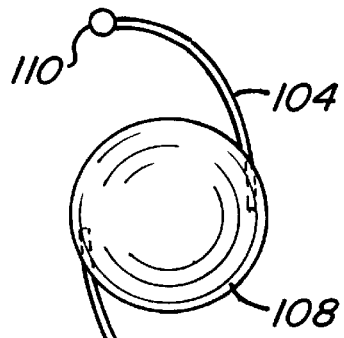
FIGS. 12 to 14 illustrate an embodiment wherein flexible or filament type loop haptics extend oppositely from an optic and having at the end of each a knob or protuberance, FIGS. 13 and 14 showing the correct manner of engagement of the loop end portion and knob in the cul-de-sac of the capsular bag for peripheral fixation in the juncture of the posterior capsule and the anterior capsular remnant by fibrosis, and FIG. 14 showing an incorrect engagement of an improperly designed end portion of the loop haptic.
Figure 13:
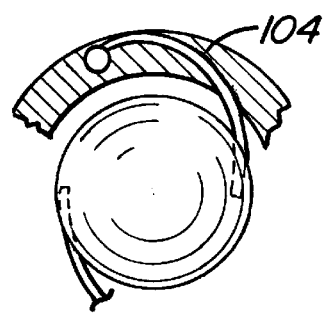
Figure 14:
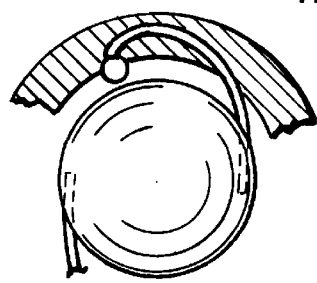

FIGS. 12–14 illustrate embodiments wherein flexible or filamentary loop haptics 104, 106 of generally arcuate configuration extend oppositely from an optic 108. Each loop haptic has at its end a knob or protuberance 110 somewhat similar to that shown in FIG. 8A. The loop haptics extend into the periphery of the bag between the anterior remnant and the posterior capsule to fixate the haptics and prevent movement of the knobs through fibrosis-defined tunnels defined about the loops. FIGS. 13 and 14 illustrate respectively the correct manner for the loop haptic to be oriented to engage the bag periphery wherein a portion of the loop and the knob engage the bag periphery. FIG. 14 shows an undesirable disposition of the loop haptic and knob in the fibrosis which does not provide optimum and desirable engagement with the bag periphery.

Figure 15:
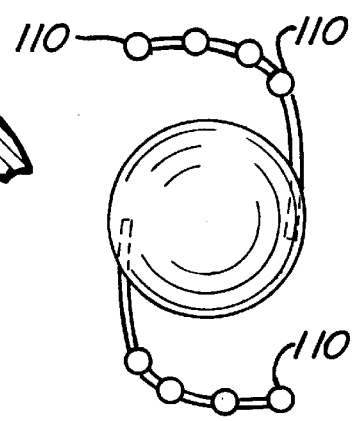
FIG. 15 shows an embodiment embodying features of the embodiment of FIG. 12, and having a plurality of knobs spaced apart on oppositely extending resilient loop haptics for improved engagement in the cul-de-sac of the periphery between the anterior remnant and the posterior capsule.

FIG. 15 illustrates an embodiment which is similar to that of FIGS. 12 and 13 except that a plurality of knobs or protuberances 110, similar to that of FIG. 8A, are positioned in spaced relation along the loop haptics to provide improved fixation of the loop haptic in the peripheral cul-de-sac of the bag.

FIGS. 16 and 16A show an embodiment having a haptic comprising two half disk-shaped members 112 from which extend a plurality of loop haptic portions 114. The edge of the disk-shaped portions and the loops are adapted to fit in the peripheral portion of the bag between the capsular remnant and the posterior capsule to fixate the haptic.

FIGS. 17 and 17A illustrate an embodiment which has a disk haptic portion 116 on which are mounted and from which extend a plurality of filament haptic portions 118 of generally arcuate configuration at the end of each of which is disposed a knob or protuberance 120. The loop haptic portions and the knobs serve the purposes outlined relative to embodiments earlier described.

FIG. 18 is an embodiment having a disk haptic 124 wherein are integrally formed peripheral inclined prong portions 126 extending somewhat tangentially with knobs at the ends thereof adapted to fit within the periphery of the bag between the anterior capsular remnant and the posterior bag for engagement with the periphery for the formation of fibrosis thereabout for the purposes earlier described.

Figure 28:
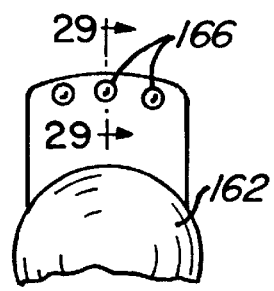

FIG. 19 is an embodiment having a disk haptic 130 on the periphery of which are disposed a plurality of knobs 132, such as the knobs of FIG. 28, to serve the purposes earlier described in relation to other embodiments.

FIG. 20 is an embodiment having a disk haptic 134 with a plurality of circular openings 136 defined in its distal peripheral portion, the haptic periphery and these openings become engaged with fibrosis to serve the purposes earlier described.

FIG. 21 shows an embodiment similar to that of FIG. 20, with slot-shaped openings 138 defined in disk haptic 140.

FIG. 22 is somewhat similar to the embodiments of FIGS. 19 and 21, and has slot-shaped openings 138 interspersed with knobs 140 in its disk peripheral edge portion.

Figure 23:
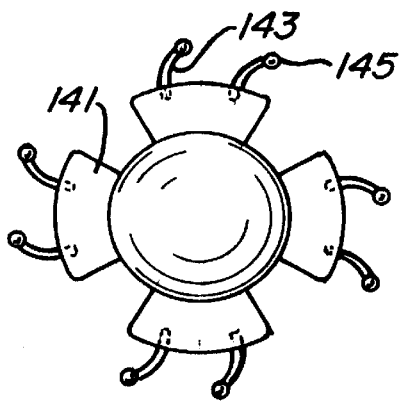
FIG. 23 shows an embodiment wherein disk haptic portions extend outwardly from an optic and flexible loop haptic elements with protuberances thereon extend from the edges of the disk portions in inclined directions opposite from the directions of loop haptics of certain other embodiments.

FIG. 23 shows an embodiment wherein disk haptic portions 141 extend outwardly from an optic, and extending from their distal edge portions are a plurality of flexible loop haptic elements 143 with protuberances 145 thereon for engagement in the peripheral edge portion of the capsular bag for fixation of the haptic and centration of the optic.

Figure 24:
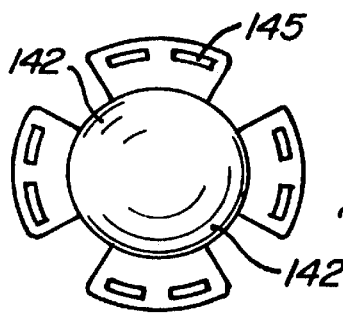
FIGS. 24 to 26 illustrate embodiments wherein a plurality of plate-type haptics are spaced about an optic, FIG. 24 showing slot openings in the existing portions of the haptics, FIG. 25 showing a plurality of knobs at the distal portion of each plate-type haptic, and FIG. 26 showing both slot-type openings and a knob in the distal portion of each plate-type haptic.
Figure 25:
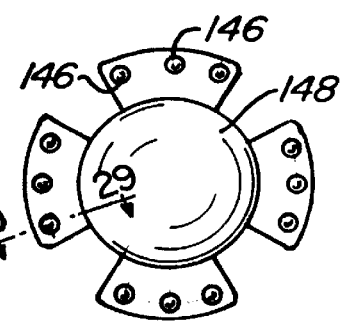
Figure 29:
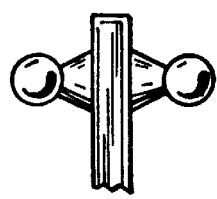
FIG. 29 is a sectional view taken at line 29—29 in FIG. 28.

FIGS. 24 and 25 show embodiments each having four plate haptics 142 extending from and equispaced about an optic 144, and having defined in their peripheral portions slot-shaped openings 145, the haptic edge portion and the openings being extensible in the bag periphery for purposes earlier described; the embodiment of FIG. 25 has similarly equispaced haptics extending from an optic 148, each haptic having a plurality of knobs like those of FIG. 29 on its peripheral portion, the knobs and haptic edge portions serving the purposes earlier described.

Figure 26:
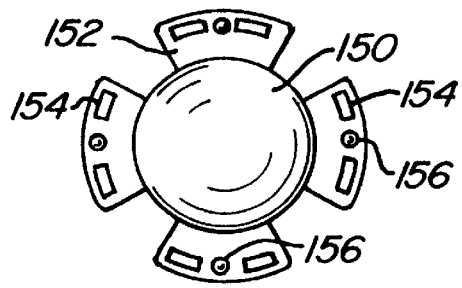

The FIG. 26 embodiment is similar to the embodiment of FIGS. 24 and 25, with an optic 150 having four equispaced haptics 152 extending therefrom, each having slot-shaped openings 154 therein and a knob 156 thereon.

Figure 27:
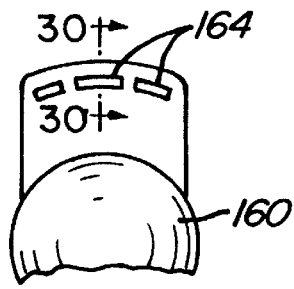
FIGS. 27 and 28 show embodiments wherein plate-type haptics extend oppositely from an optic, only one such haptic being shown, FIG. 27 showing an embodiment wherein slot-type openings are defined in the distal edge portion of such haptic element, and FIG. 28 showing knobs or protuberances disposed on the distal portion of said plate-type haptic.

FIGS. 27 and 28 illustrate embodiments wherein plate-type haptics extend oppositely from optic 160 in FIG. 27, and from optic 162 in FIG. 28, the FIG. 27 embodiment having a haptic with slot-shaped openings 164 in its distal portion, and the haptics (lower one not shown) of FIG. 28 having a plurality of knobs 166 in its peripheral portion, the slots and the knobs serving the purposes earlier described.

FIG. 29 is a partial sectional view taken at line 29—29 in FIG. 28, and

Figure 30:
FIG. 30 is a sectional view taken at line 30—30 in FIG. 27.

FIG. 30 is a partial sectional view taken at line 30—30 in FIG. 27.

Thus there have been shown and described novel intraocular lenses with fixated haptics which fulfill all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. An intraocular lens for implanting within a human eye, the eye having a natural capsular bag attached about its perimeter to the ciliary muscle of the eye and from which the natural lens matrix has been removed, the bag including an elastic posterior capsule urged anteriorly by vitreous pressure and an anterior capsule opening circumferentially surrounded by a capsular remnant fused by fibrose tissue to the posterior capsule, said lens implant comprising:

an intraocular lens having anterior and posterior sides and including a central optic, and generally rectilinear plate haptics joined to and extending oppositely from the optic, and distal step prongs extending outwardly transversely of the haptic and having knob protuberances thereon, said haptic distal end portion is positionable in the periphery of the capsular bag between the anterior remnant and the posterior capsule, and is adapted, sized and configurated to engage fibrosed tissue of said fibrosis to fixate the haptic and retain said knob protuberances against movement relative to tunnels defined by fibrosis about proximally inward haptic portions of relatively reduced size.

2. An accommodating intraocular lens comprising:

a lens having normally anterior and posterior sides as disposed in an eye, said lens including an optic and two plate haptics extending from their respective proximal ends oppositely from the optic, at least one of said haptics having a distal prong extending transversely outwardly therefrom and having thereon a substantially globular knob protuberance extending outwardly from at least one of the anterior and posterior sides of the prong for fixation in an anterior natural capsule of the eye, said lens is adapted for implanting in a human eye within a natural capsular bag in the eye attached about its perimeter to the ciliary muscle of the eye and including an elastic posterior capsule which is urged anteriorly by vitreous pressure in the eye and an anterior capsule opening bounded circumferentially by an anterior capsule remnant that fuses to the posterior capsule by fibrosis during a postoperative fibrosis period induced by application of drug to maintain ciliary muscle relaxation, during which period said bag and remnant shrink, said remnant being tautly stretched by relaxation of the ciliary muscle and relaxed by contraction of the ciliary muscle after said fibrosis period, said lens is adapted to be implanted in said bag while said ciliary muscle is in its relaxed state and in an implanted position wherein said optic is aligned with said anterior capsule opening and said haptics are disposed between said posterior capsule and said anterior capsule remnant, whereby said fibrosis occurs and defines respective tunnels about portions of said respective haptics and said optic is urged posteriorly against said posterior capsule during fibrosis, and after fibrosis is complete relaxation of the ciliary muscle effects posterior movement of said optic to a distant vision position and contraction of the ciliary muscle effects anterior accommodation movement of the optic, and said plate haptics having distal end portions sized and adapted to substantially prevent entry thereof into one or more tunnels formed by fibrosis about proximally adjacent haptic portions, whereby said distal haptic end portions are fixated and retained against movement in the proximal direction toward the optic.

3. An accommodating intraocular lens according to claim 2, wherein plate haptics extend oppositely from the optic, and having step prong portions extending transversely outwardly from said plate haptics and oppositely from each other, said haptics having arcuate distal end edge portions adapted to engage in the capsular bag.

4. An accommodating intraocular lens according to claim 3, wherein a distal prong on each haptic has said substantially globular knob protuberance on its outer end, the prongs and protuberances being adapted to be disposed in the bag periphery between the posterior capsule and the anterior capsule remnant.

5. An accommodating intraocular lens according to claim 2, wherein the plate haptics extend oppositely from an optic, each of the plate haptics having said substantially globular knob protuberance disposed on its distal edge portion and extending anteriorly and posteriorly of the haptic with respect to the eye.

6. An intraocular lens according to claim 2, wherein:

said prongs with said knob protuberances on the ends thereof extending therefor oppositely from side edges of the distal portions of the haptics, said prongs having arcuate distal edges adapted to engage in the capsular bag.

7. An intraocular lens according to claim 6, wherein prong protuberances extend outwardly from each side of the distal portions of two plate haptics extending oppositely from the optic.

8. An intraocular lens according to claim 2, and wherein the at least one plate haptic is longitudinally tapered and has a wide distal end portion having an arcuate edge and said prongs having arcuate edges complementary with the haptic arcuate edge to fit in the capsular bag periphery.

9. An intraocular lens according to claim 2, wherein said two haptics extend oppositely from the optic, the haptics being tapered and defining end portions with the knob protuberances thereon.

* * * * *